US00PP36250P2

(12) United States Plant Patent
Jiang

(10) Patent No.: US PP36,250 P2
(45) Date of Patent: Nov. 12, 2024

(54) ***PELARGONIUM* PLANT NAMED 'PEQZ0107'**

(50) Latin Name: ***Pelargonium* x *interspecific***
Varietal Denomination: PEQZ0107

(71) Applicant: SYNGENTA CROP PROTECTION AG, Basel (CH)

(72) Inventor: Li Jiang, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,059

(22) Filed: May 23, 2024

(51) Int. Cl.
*A01H 5/02* (2018.01)
*A01H 6/42* (2018.01)

(52) U.S. Cl.
USPC ..... Plt./327

(58) Field of Classification Search
USPC ..... Plt./327
CPC . A01H 5/02; A01H 5/00; A01H 6/425; A01H 6/42
See application file for complete search history.

(56) References Cited

U.S. PATENT DOCUMENTS

PP33,078 P2 * 5/2021 Snijder ..... A01H 5/02 Plt./327

* cited by examiner

*Primary Examiner* — June Hwu
(74) *Attorney, Agent, or Firm* — Dale Skalla

(57) ABSTRACT

A new *Pelargonium* plant named 'PEQZ0107' particularly distinguished by salmon-colored semi-double flower inflorescences held above medium green foliage, on a mounding plant.

1 Drawing Sheet

Latin name of the genus and species of the plant claimed: *Pelargonium* x interspecific.

Varietal denomination: 'PEQZ0107'.

BACKGROUND OF THE NEW PLANT

The present invention comprises a new *Pelargonium*, botanically known as *Pelargonium* interspecific, and hereinafter referred to by the variety name 'PEQZ0107'.

'PEQZ0107' is a product of a planned breeding program. The new cultivar 'PEQZ0107' has salmon colored and semi-double flower inflorescences with a held above medium green foliage, on a mounding plant.

'PEQZ0107' originates from a hybridization in a controlled breeding program made in March 2019 in a greenhouse in Amatitlán, Guatemala. The female parent was a patented, proprietary plant of P. x interspecific parentage identified as 'PEQZ0033', described in U.S. Plant Pat. No. 29,484, with a lighter salmon colored flowers and a similar mounding habit when compared to 'PEQZ0107'.

The male parent of 'PEQZ0107' was a patented, proprietary plant of P. x interspecific parentage, identified as 'PEQZ0011', described in U.S. Plant Pat. No. 28,488 with scarlet-colored florets, a more distinct leaf zone, and a less vigorous mounding plant habit when compared to 'PEQZ0107'. The resultant seed was sown in September 2019.

'PEQZ0107' was selected as one flowering plant within the progeny of the stated cross in December 2019 in a greenhouse in Gilroy, California.

The first act of asexual reproduction of 'PEQZ0107' was accomplished when vegetative cuttings were propagated from the initial selection in January 2020 in a greenhouse in Gilroy, California.

BRIEF SUMMARY OF INVENTION

Horticultural examination of plants grown from cuttings of the plant initiated in July 2020 in Gilroy, California, and continuing thereafter, has demonstrated that the combination of characteristics as herein disclosed for 'PEQZ0107' are firmly fixed and are retained through successive generations of asexual reproduction.

'PEQZ0107' has not been observed under all possible environmental conditions. The phenotype may vary significantly with variations in environment such as temperature, light intensity, and day length.

A Plant Breeder's Right for this cultivar has not yet been applied for. 'PEQZ0107' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0107' with colors being as true as possible with an illustration of this type.

Figure 1:
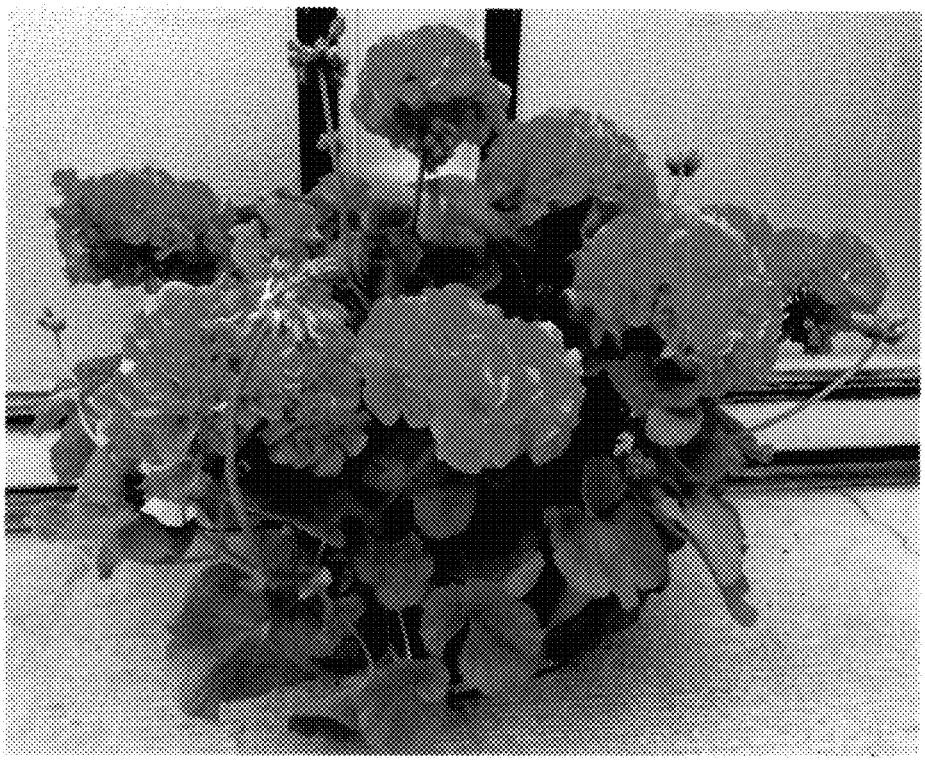
Figure 2:
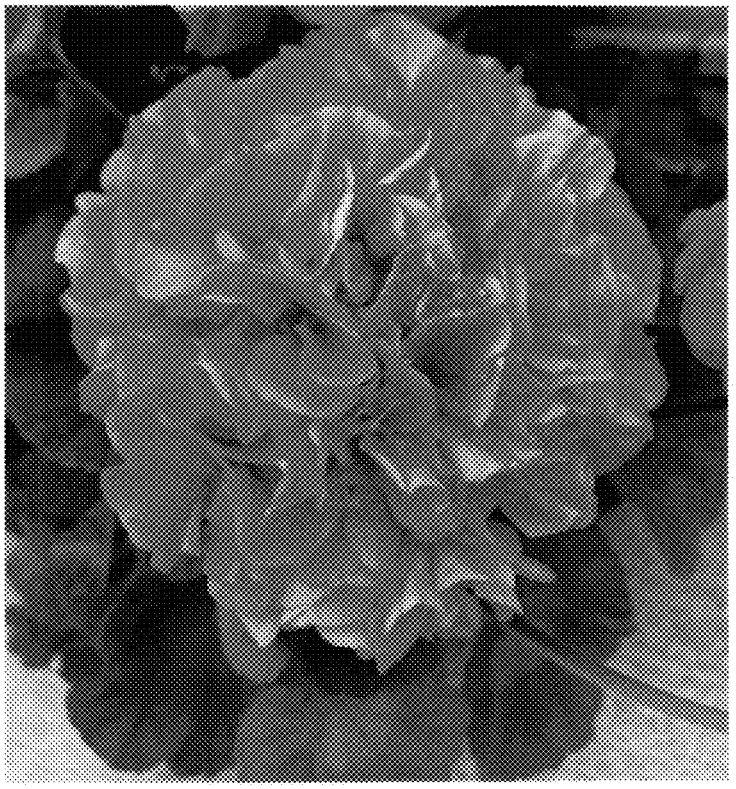

The photographic drawings show in FIG. 1, one flowering plants of the new variety and in FIG. 2, a close-up of an inflorescence.

DETAILED BOTANICAL DESCRIPTION

The plant descriptions and measurements were taken in Gilroy, California in April 2024 under natural light. These plants were approximately 17 weeks old and were grown in quart size pots, in a greenhouse trial. The plants shown in the photographs were about 17 weeks old growing in a quart pot in a greenhouse. The photographs were taken in April 2024.

Color references are made to The Royal Horticultural Society Colour Chart (RHS) of 2015.

TABLE 1

DIFFERENCES BETWEEN THE NEW VARIETY 'PEQZ0107' AND A MOST SIMILAR VARIETY

| | 'PEQZ0107' | 'PEQZ0099' (U.S. Plant Pat. No. 35,493) |
|---|---|---|
| Color of upper surface petals: | Vivid red, RHS 52A | Moderate reddish orange, RHS 41C, fading to RHS 57A at the upper half and fading to RHS 62D at the lower half |
| Color of stem: | Close to RHS 146A and RHS 146B | Close to RHS 143B |
| Pedicel color: | From bottom to top, moderate yellow green RHS 146C to orange red RHS N34C | Basal part RHS 143B |

PLANT

Form, growth and habit: Mounding growth habit.
Plant height: 20-24 cm.
Plant height (inflorescence included): 28-32 cm.
Plant width: 35-60 cm.

ROOTS

Number of days to initiate roots: 15-18 days at about 22 degrees C.
Number of days to produce a rooted cutting: 21-23 days at 22 degrees C.
Type: Fine, fibrous, free branching.
Color: RHS N155B but whiter.

FOLIAGE

Variegation: Sparse on ends of leaves.
Immature leaf, color upper surface: Between RHS 137A and RHS 137B.
Immature leaf, lower surface: RHS 146B.
Mature leaf, color upper surface: Between RHS 137A and RHS 137B.
Mature leaf, color lower surface: RHS 147B.
Length: 5.5-7 cm.
Width: 9-12 cm.
Shape: Cordate.
Base shape: Cordate.
Sinus of mature leaf: Wide.
Leaf base openness: Variable, immature leaves concave, mature leaves open.
Apex shape: Rounded.
Margin: Wavy, undulate margins.
Texture upper side: Hirsute.
Texture lower side: Hirsute.
Leaf zonation color: RHS NN137B.
Color of veins, upper surface: RHS 137B.
Color of veins, lower surface: RHS 146D, distinct.
Pattern of veining: Palmate.
Petiole color: Between RHS 146B and RHS 146C.
Petiole length: 5-9 cm.
Diameter of petiole: 0.2-0.4 cm.
Texture: Hirsute.

STEM

Quantity of branches: 5-9.
Color of stem: Close to RHS 146A and RHS 146B.
Anthocyanin coloration of stem: Little to no anthocyanin coloration.
Length of stem: 9-20 cm.
Diameter: 0.5 cm.
Length of internodes: 1-4 cm.
Texture: Sparsely hirsute, pilose, glandular hairs.

PEDUNCLE

Color of peduncle: RHS 146B and 146C.
Length of peduncle: 13-18 cm.
Peduncle diameter: 0.3-0.5 cm.
Texture: Hirsute.
Anthocyanin coloration of peduncle: Little to no anthocyanin coloration.

PEDICEL

Color of pedicel: RHS 146C with RHS N34C closer to flower.
Length of pedicel: 1-2.5 cm.
Diameter of pedicel: 0.2 cm.
Texture: Sparsely pilose.
Pedicel swelling: Minimal to no swelling.

BUD (just before opening)

Color: RHS 43B and RHS 43C.
Length: 1.2-2 cm.
Width: 0.6-1 cm.
Shape: Elliptical.

INFLORESCENCE

Type: Umbel; semi-spherical or nearly semi-spherical.
Lastingness of individual flowers: 7-9 days at 18° C. temperature.
Number of inflorescences per plant: 6-12, with 5-12 immature umbels in various stages.
Average total number of buds: 30.
Fragrance: None.
Umbel diameter: 6-10 cm.
Umbel depth: 6-8 cm.

COROLLA

Form: Semi-double.
Number of petals: 8.
Diameter of flower: 4.5-5.2 cm.
Depth of flower: 1-2 cm.
Side view shape: Concave.
Color upper petals, upper surface: RHS 52A.
Color upper petals, lower surface: Between RHS 52A and RHS 52B.
Length of upper petals: 2.8-3.0 cm.
Width of upper petals: 2.1-2.6 cm.
Color lower petals, upper surface: RHS 52A.
Color lower petals, lower surface: RHS 55B.
Markings on upper petals: None.
Markings on lower petals: None.

Length of lower petals: 2.7-3 cm.
Width of lower petals: 2.0-2.2 cm.
Petal shape: Obovate to spathulate.
Apex shape: Rounded.
Margin: Slightly dentate.
Base: Attenuate.
Petal texture: Papillose on both surfaces.

CALYX

Number of sepals: 5.
Color of sepals: RHS 146B with RHS 185B.
Length of sepals: 1.2-1.3 cm.
Width of sepals: 0.2-0.6 cm.
Sepal shape: Lanceolate to linear.
Apex shape: Acute.
Margins: Mostly fused.
Texture, upper surface: Hirsute.
Lower surface: Hirsute.
Sepal flexing: Mostly unflexed sepals. The narrowest sepals might flex moderately.

REPRODUCTIVE ORGANS

GYNOECIUM

Pistil: RHS 60C.
Length: 0.5 cm.
Style color: RHS 59D.
Style length: 0.3 cm.
Stigma color: RHS 53C.
Ovary color: RHS 143D.
Ovary length: 0.4-0.6 cm.
Ovary diameter: 0.3 cm.

ANDROECIUM

Number of stamens: 3-5 with 2-3 staminodes.
Color of filaments: RHS 157D.
Length filaments: 0.4-0.8 cm.
Anther color: RHS 48A.
Length of anthers: 0.2-0.4 cm.
Color of pollen: RHS 171B.
Pollen amount: Scarce.
Fertility/seed set: Has not been determined to date.
Disease/pest resistance: Has not been determined to date.

What is claimed is:

1. A new and distinct variety of *Pelargonium* plant named 'PEQZ0107' substantially as illustrated and described herein.

* * * * *